United States Patent
Park et al.

(10) Patent No.: US 9,313,781 B2
(45) Date of Patent: Apr. 12, 2016

(54) METHOD AND DEVICE FOR TRANSMITTING DOWNLINK CONTROL SIGNAL IN WIRELESS COMMUNICATION SYSTEM

(75) Inventors: Kyu Jin Park, Anyang-si (KR); Han Gyu Cho, Anyang-si (KR); Seung Hyun Kang, Anyang-si (KR)

(73) Assignee: LG Electronics Inc., Seoul (KR)

( * ) Notice: Subject to any disclaimer, the term of this patent is extended or adjusted under 35 U.S.C. 154(b) by 110 days.

(21) Appl. No.: 13/990,664

(22) PCT Filed: Dec. 1, 2011

(86) PCT No.: PCT/KR2011/009280
§ 371 (c)(1),
(2), (4) Date: Jul. 17, 2013

(87) PCT Pub. No.: WO2012/074318
PCT Pub. Date: Jun. 7, 2012

(65) Prior Publication Data
US 2013/0286918 A1    Oct. 31, 2013

Related U.S. Application Data

(60) Provisional application No. 61/419,215, filed on Dec. 2, 2010.

(51) Int. Cl.
*H04W 72/04* (2009.01)
*A01N 37/02* (2006.01)

(52) U.S. Cl.
CPC ............. *H04W 72/042* (2013.01); *A01N 37/02* (2013.01)

(58) Field of Classification Search
CPC .. H04W 52/02; H04W 52/0216; H04W 84/12

USPC ........................................................ 370/311
See application file for complete search history.

(56) References Cited

U.S. PATENT DOCUMENTS

2007/0259673 A1   11/2007   Willars et al.
2010/0246427 A1   9/2010   Gheorghiu et al.
(Continued)

FOREIGN PATENT DOCUMENTS

CN   101588625 A   11/2009
CN   101796870 A   8/2010
WO   WO 2009/129897 A1   10/2009

OTHER PUBLICATIONS

Motorola: "SPS Scheduling for SID VoIP Packets", R2-104001, Jun. 28-Jul. 2, 2010, Stockholm, Sweden (see the entire document http://www.3gpp.org/ftp/tsg_ran/WG2_RL2/TSGR2_70bis/Docs/).
(Continued)

*Primary Examiner* — Mark Rinehart
*Assistant Examiner* — Peter Solinsky
(74) *Attorney, Agent, or Firm* — Dentons US LLP

(57) ABSTRACT

Provided are a method and a device for transmitting a downlink control signal in a wireless communication system. A base station sets a transmission/reception (Tx/Rx) period ($T_{SPS}$) on the basis of the type of a machine to machine (M2M) application, transmits said set Tx/Rx period to an M2M device, and performs a permanent scheduling for said M2M device on the basis of said set Tx/Rx period. Alternatively, the base station transmits a first downlink control signal that is allocated for an M2M group, which includes a plurality of M2M devices, to an M2M device that is included in said M2M group, and transmits, to said M2M device, a second downlink control signal that is specific to and allocated to said M2M device.

9 Claims, 11 Drawing Sheets

| UE IDENTIFICATION FIELD | GROUP-COMMON CONTROL INFORMATION | UE-SPECIFIC CONTROL INFORMATION FOR UE #1 | UE-SPECIFIC CONTROL INFORMATION FOR UE #2 | ... | UE-SPECIFIC CONTROL INFORMATION FOR UE #N | CRC (MASKED TO GROUP ID) |
|---|---|---|---|---|---|---|

(56) References Cited

U.S. PATENT DOCUMENTS

| | | | |
|---|---|---|---|
| 2011/0069653 A1* | 3/2011 | Wang et al. .................... | 370/312 |
| 2011/0086614 A1* | 4/2011 | Brisebois ................. | H04K 3/42 |
| | | | 455/411 |
| 2011/0159914 A1* | 6/2011 | Chen et al. .................... | 455/522 |
| 2011/0171985 A1* | 7/2011 | Papasakellariou et al. ... | 455/509 |
| 2011/0201344 A1* | 8/2011 | Ryu ........................ | H04W 4/08 |
| | | | 455/450 |
| 2011/0216773 A1* | 9/2011 | Vegesna et al. ............ | 370/395.4 |
| 2011/0252235 A1* | 10/2011 | Dolan et al. ................. | 713/168 |
| 2012/0083283 A1* | 4/2012 | Phan et al. .................... | 455/450 |
| 2012/0122463 A1* | 5/2012 | Chen et al. .................... | 455/450 |
| 2012/0207123 A1* | 8/2012 | Seo et al. ...................... | 370/329 |
| 2012/0300655 A1* | 11/2012 | Lee et al. ...................... | 370/252 |
| 2013/0039246 A1* | 2/2013 | Park et al. ..................... | 370/311 |
| 2013/0195041 A1* | 8/2013 | Papasakellariou et al. ... | 370/329 |

OTHER PUBLICATIONS

Nokia Siemens Networks, Nokia Corporation: "Semi-Persistent Scheduling in Carrier Aggregation", R2-101987, Apr. 12-16, 2010, Beijing, China (see the entire document http://www.3gpp.org/ftp/tsg_ran/WG2_RL2/TSGR2_69bis/Docs/).

* cited by examiner

FIG. 8

(a) | FREQUENCY HOPPING FLAG | RESOURCE BLOCK ASSIGNMENT | MCS | TPC COMMAND | DMRS CYCLIC SHIFT | UL INDEX | DAI |

(a) | FREQUENCY HOPPING FLAG | RESOURCE BLOCK ASSIGNMENT | TPC COMMAND | DMRS CYCLIC SHIFT | UL INDEX | DAI |

FIG. 9

| UE IDENTIFICATION FIELD | GROUP-COMMON CONTROL INFORMATION | UE-SPECIFIC CONTROL INFORMATION FOR UE #1 | UE-SPECIFIC CONTROL INFORMATION FOR UE #2 | ... | UE-SPECIFIC CONTROL INFORMATION FOR UE #N | CRC (MASKED TO GROUP ID) |

METHOD AND DEVICE FOR TRANSMITTING DOWNLINK CONTROL SIGNAL IN WIRELESS COMMUNICATION SYSTEM

This Application is a 35 U.S.C. §371 National Stage Entry of International Application No. PCT/KR2011/009280, filed Dec. 1, 2011 and claims the benefit of U.S. Provisional Application No. 61/419,215, filed Dec. 2, 2010, all of which are incorporated by reference in their entirety herein.

BACKGROUND OF THE INVENTION

1. Field of the Invention

The present invention relates to wireless communications and, more particularly, to a method and apparatus for transmitting a downlink control signal in a wireless communication system.

2. Related Art

As machine type communication (MTC) or machine to machine (M2M) communication is recently introduced, a variety of scenarios are required. The M2M communication is one type of data communication including one or more entities that do not require an interaction with people. That is, the M2M communication refers to a concept in which a machine device not a mobile station (MS) used by people performs communication using a network, such as an existing GSM/EDGE radio access network (GERAN), a universal mobile telecommunications system (UMTS), or $3^{rd}$ generation partnership project (3GPP) long-term evolution (LTE). Pieces of information can be exchanged without the intervention of people between subscriber stations or a subscriber station and a server through the M2M communication. A machine device used in the M2M communication can be called an MTC device or an M2M device, and the M2M device is various like a vending machine and a machine for measuring the water level of a dam. That is, the M2M communication can be widely applied to various fields. Cellular M2M applications applicable to the M2M communication can include secured access surveillance, health care, smart grid, tracking/tracing recovery, remote maintenance control, automotives, public safety, mobile payment, and consumer electronics.

The MTC can mean many M2M devices coupled through autonomously integrated communication techniques and systems and having various types of quality of service (QoS). The M2M device has different features from a common MS, and service optimized for M2M can be different from service optimized for human type communication (HTC). Cellular M2M requirements can include 1) low power consumption for an M2M device having a limited battery, 2) the support of many M2M devices within a cell, 3) high reliability within a cellular environment, 4) a time-controlled operation, 5) a wider range for mobility for various cellular M2M applications, and 6) the efficient support of the transmission of a small burst, as compared with current mobile network communication service.

As M2M communication is introduced, a base station (BS) needs to support connection between many M2M devices and scheduling for the transmission of a small amount of data. To this end, a BS needs to transmit a downlink control signal to many M2M devices, which can result in overload for a downlink control channel. Accordingly, there is a need for an efficient method of assigning a downlink control channel for an M2M device.

SUMMARY OF THE INVENTION

The present invention provides a method and apparatus for transmitting a downlink control signal in a wireless communication system. The present invention proposes a method of performing persistent scheduling for many M2M devices according to an M2M application. Furthermore, the present invention proposes a method of defining a group downlink control information (DCI) format based on an M2M group including a plurality of M2M devices.

In an aspect, a method of performing a persistent scheduling on a machine to machine (M2M) device in a wireless communication system is provided. The method includes setting a transmission/reception (Tx/Rx) cycle $T_{SPS}$ based on a type of an M2M application, transmitting the set Tx/Rx cycle to the M2M device, and performing a persistent scheduling on the M2M device based on the set Tx/Rx cycle.

The Tx/Rx cycle may be negotiated or requested by the M2M device.

The Tx/Rx cycle may be transmitted by L1/L2 control signaling or higher layer signaling.

The Tx/Rx cycle may be updated by higher layer signaling.

The method may further include setting a discontinuous reception (DRX) cycle that is an interval in which the M2M device does not communicate with a base station based on the Tx/Rx cycle.

In another aspect, a method of transmitting a downlink control signal in a wireless communication system is provided. The method includes transmitting a first downlink control signal assigned to a machine to machine (M2M) group, comprising a plurality of M2M devices, to an M2M device included in the M2M group, and transmitting a second downlink control signal, specifically assigned to the M2M device, to the M2M device.

The first downlink control signal and the second downlink control signal may be transmitted through a group downlink control information (DCI) format.

The group DCI format may comprise a user equipment (UE) identification field to identify the M2M device.

The group DCI format may comprise cyclic redundancy check (CRC) masked to an identifier (ID) of the M2M group.

The group DCI format may comprise control information specially assigned to other M2M devices included in the M2M group.

The method may further include configuring a group multicasting DCI format for scheduling group-common multicast information assigned to the M2M group in common.

The first downlink control signal may be a DCI format comprising group-specific resource assignment information, and the second downlink control signal may be determined implicitly or explicitly.

In another aspect, a machine to machine (M2M) device in a wireless communication system is provided. The M2M device includes a radio frequency (RF) unit for transmitting or receiving a radio signal, and a processor connected to the RF unit, and configured for receiving a first downlink control signal assigned to an M2M group, comprising a plurality of M2M devices, from a base station, receiving a second downlink control signal, specifically assigned to the M2M device itself, from the base station, and transmitting uplink through a channel scheduled based on the first downlink control signal and the second downlink control signal.

An efficient downlink control channel for an M2M device can be assigned.

BRIEF DESCRIPTION OF THE DRAWINGS

FIG. 8 shows an example of a reduced DCI format according to the proposed method of transmitting a downlink control signal.

FIG. 9 shows an example of a group DCI format according to the proposed method of transmitting a downlink control signal.

DESCRIPTION OF EXEMPLARY EMBODIMENTS

The following technique may be used for various wireless communication systems such as code division multiple access (CDMA), a frequency division multiple access (FDMA), time division multiple access (TDMA), orthogonal frequency division multiple access (OFDMA), single carrier-frequency division multiple access (SC-FDMA), and the like. The CDMA may be implemented as a radio technology such as universal terrestrial radio access (UTRA) or CDMA2000. The TDMA may be implemented as a radio technology such as a global system for mobile communications (GSM)/general packet radio service (GPRS)/enhanced data rates for GSM evolution (EDGE). The OFDMA may be implemented by a radio technology such as institute of electrical and electronics engineers (IEEE) 802.11 (Wi-Fi), IEEE 802.16 (WiMAX), IEEE 802.20, E-UTRA (evolved UTRA), and the like. IEEE 802.16m, an evolution of IEEE 802.16e, provides backward compatibility with a system based on IEEE 802.16e. The UTRA is part of a universal mobile telecommunications system (UMTS). 3GPP (3rd generation partnership project) LTE (long term evolution) is part of an evolved UMTS (E-UMTS) using the E-UTRA, which employs the OFDMA in downlink and the SC-FDMA in uplink. LTE-A (advanced) is an evolution of 3GPP LTE.

Hereinafter, for clarification, LTE-A will be largely described, but the technical concept of the present invention is not meant to be limited thereto.

Figure 1:
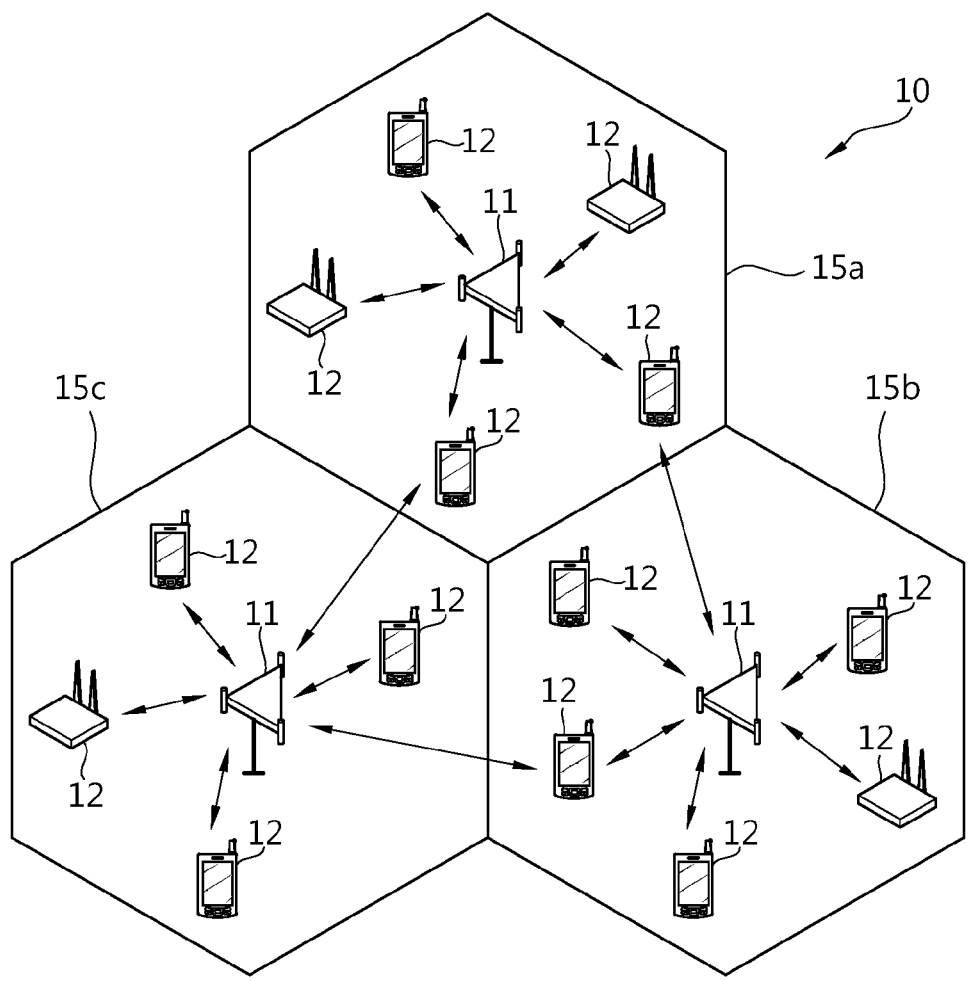
FIG. 1 shows a wireless communication system.

FIG. 1 shows a wireless communication system.

The wireless communication system 10 includes at least one base station (BS) 11. Respective BSs 11 provide a communication service to particular geographical areas 15a, 15b, and 15c (which are generally called cells). Each cell may be divided into a plurality of areas (which are called sectors). A user equipment (UE) 12 may be fixed or mobile and may be referred to by other names such as MS (mobile station), MT (mobile terminal), UT (user terminal), SS (subscriber station), wireless device, PDA (personal digital assistant), wireless modem, handheld device. The BS 11 generally refers to a fixed station that communicates with the UE 12 and may be called by other names such as eNB (evolved-NodeB), BTS (base transceiver system), access point (AP), etc.

In general, a UE belongs to one cell, and the cell to which a UE belongs is called a serving cell. A BS providing a communication service to the serving cell is called a serving BS. The wireless communication system is a cellular system, so a different cell adjacent to the serving cell exists. The different cell adjacent to the serving cell is called a neighbor cell. A BS providing a communication service to the neighbor cell is called a neighbor BS. The serving cell and the neighbor cell are relatively determined based on a UE.

This technique can be used for downlink or uplink. In general, downlink refers to communication from the BS 11 to the UE 12, and uplink refers to communication from the UE 12 to the BS 11. In downlink, a transmitter may be part of the BS 11 and a receiver may be part of the UE 12. In uplink, a transmitter may be part of the UE 12 and a receiver may be part of the BS 11.

The wireless communication system may be any one of a multiple-input multiple-output (MIMO) system, a multiple-input single-output (MISO) system, a single-input single-output (SISO) system, and a single-input multiple-output (SIMO) system. The MIMO system uses a plurality of transmission antennas and a plurality of reception antennas. The MISO system uses a plurality of transmission antennas and a single reception antenna. The SISO system uses a single transmission antenna and a single reception antenna. The SIMO system uses a single transmission antenna and a plurality of reception antennas. Hereinafter, a transmission antenna refers to a physical or logical antenna used for transmitting a signal or a stream, and a reception antenna refers to a physical or logical antenna used for receiving a signal or a stream.

Figure 2:
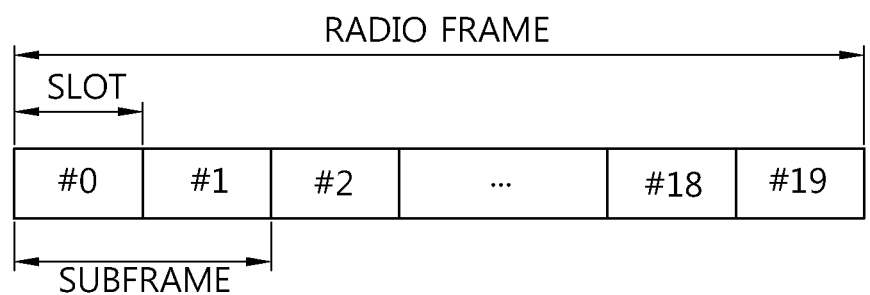
FIG. 2 shows the structure of a radio frame in 3GPP LTE.

FIG. 2 shows the structure of a radio frame in 3GPP LTE.

It may be referred to Paragraph 5 of "Technical Specification Group Radio Access Network; Evolved Universal Terrestrial Radio Access (E-UTRA); Physical channels and modulation (Release 8)" to 3GPP (3rd generation partnership project) TS 36.211 V8.2.0 (2008 March). Referring to FIG. 2, the radio frame includes 10 subframes, and one subframe includes two slots. The slots in the radio frame are numbered by #0 to #19. A time taken for transmitting one subframe is called a transmission time interval (TTI). The TTI may be a scheduling unit for a data transmission. For example, a radio frame may have a length of 10 ms, a subframe may have a length of 1 ms, and a slot may have a length of 0.5 ms.

One slot includes a plurality of orthogonal frequency division multiplexing (OFDM) symbols in a time domain and a plurality of subcarriers in a frequency domain. Since 3GPP LTE uses OFDMA in downlink, the OFDM symbols are used to express a symbol period. The OFDM symbols may be called by other names depending on a multiple-access scheme. For example, when a single carrier frequency division multiple access (SC-FDMA) is in use as an uplink multi-access scheme, the OFDM symbols may be called SC-FDMA symbols. A resource block (RB), a resource allocation unit, includes a plurality of continuous subcarriers in a slot. The structure of the radio frame is merely an example. Namely, the number of subframes included in a radio frame, the number of slots included in a subframe, or the number of OFDM symbols included in a slot may vary.

3GPP LTE defines that one slot includes seven OFDM symbols in a normal cyclic prefix (CP) and one slot includes six OFDM symbols in an extended CP.

The wireless communication system may be divided into a frequency division duplex (FDD) scheme and a time division duplex (TDD) scheme. According to the FDD scheme, an uplink transmission and a downlink transmission are made at different frequency bands. According to the TDD scheme, an uplink transmission and a downlink transmission are made during different periods of time at the same frequency band. A channel response of the TDD scheme is substantially reciprocal. This means that a downlink channel response and an uplink channel response are almost the same in a given frequency band. Thus, the TDD-based wireless communication system is advantageous in that the downlink channel response can be obtained from the uplink channel response. In the TDD scheme, the entire frequency band is time-divided for uplink and downlink transmissions, so a downlink transmission by the BS and an uplink transmission by the UE can be simultaneously performed. In a TDD system in which an uplink transmission and a downlink transmission are discriminated in units of subframes, the uplink transmission and the downlink transmission are performed in different subframes.

Figure 3:
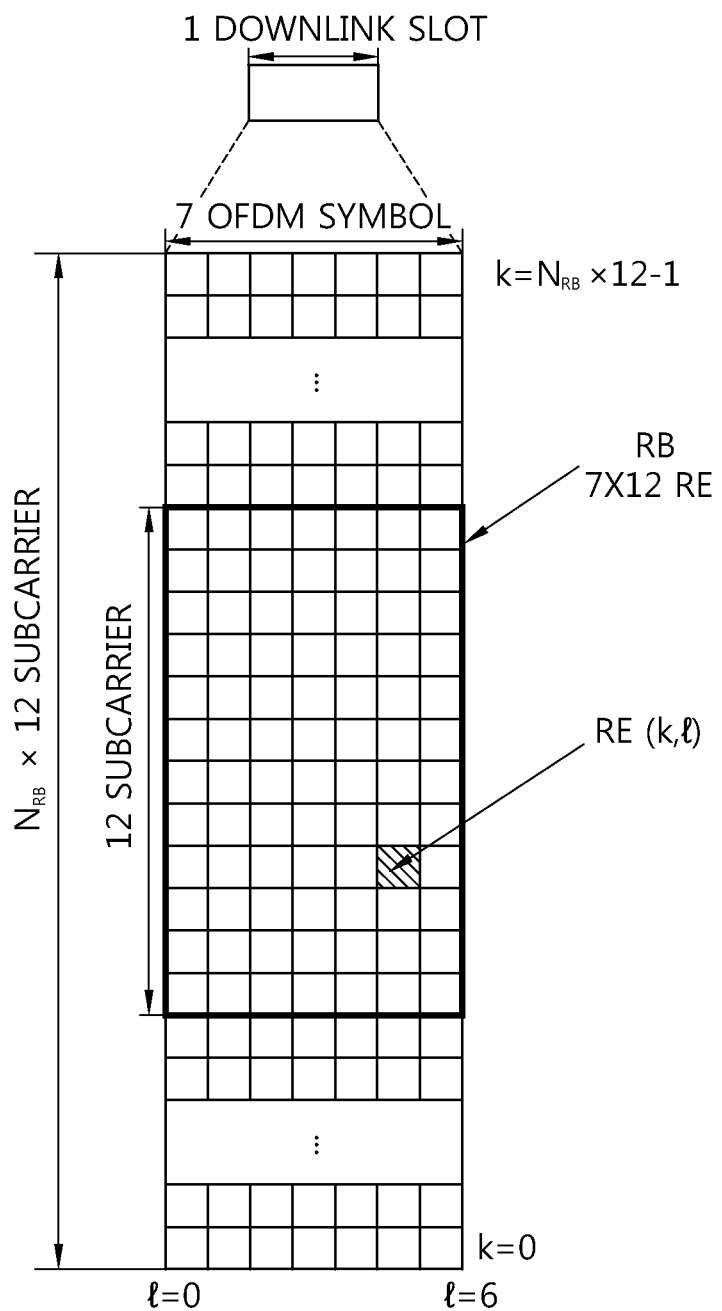
FIG. 3 shows an example of a resource grid of a single downlink slot.

FIG. 3 shows an example of a resource grid of a single downlink slot.

A downlink slot includes a plurality of OFDM symbols in the time domain and $N_{RB}$ number of resource blocks (RBs) in the frequency domain. The $N_{RB}$ number of resource blocks included in the downlink slot is dependent upon a downlink transmission bandwidth set in a cell. For example, in an LTE system, $N_{RB}$ may be any one of 60 to 110. One resource block includes a plurality of subcarriers in the frequency domain. An uplink slot may have the same structure as that of the downlink slot.

Each element on the resource grid is called a resource element. The resource elements on the resource grid can be discriminated by a pair of indexes (k,l) in the slot. Here, k (k=0, ..., $N_{RB}\times12-1$) is a subcarrier index in the frequency domain, and l is an OFDM symbol index in the time domain.

Here, it is illustrated that one resource block includes 7×12 resource elements made up of seven OFDM symbols in the time domain and twelve subcarriers in the frequency domain, but the number of OFDM symbols and the number of subcarriers in the resource block are not limited thereto. The number of OFDM symbols and the number of subcarriers may vary depending on the length of a cyclic prefix (CP), frequency spacing, and the like. For example, in case of a normal CP, the number of OFDM symbols is 7, and in case of an extended CP, the number of OFDM symbols is 6. One of 128, 256, 512, 1024, 1536, and 2048 may be selectively used as the number of subcarriers in one OFDM symbol.

Figure 4:
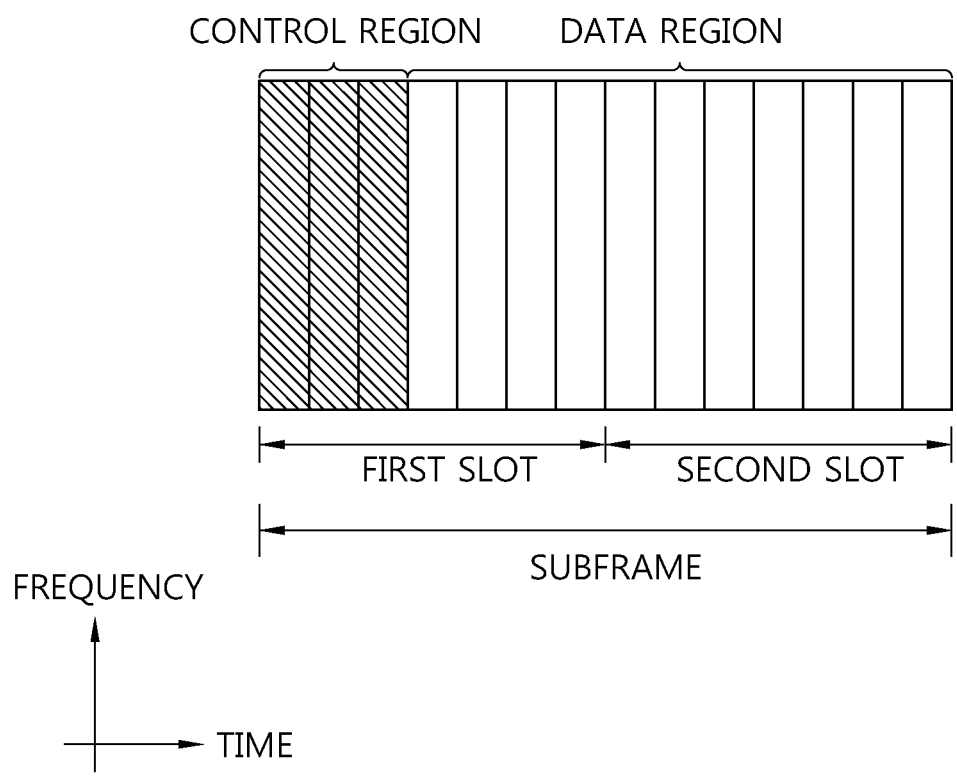
FIG. 4 shows the structure of a downlink subframe.

FIG. 4 shows the structure of a downlink subframe.

A downlink subframe includes two slots in the time domain, and each of the slots includes seven OFDM symbols in the normal CP. First three OFDM symbols (maximum four OFDM symbols with respect to a 1.4 MHz bandwidth) of a first slot in the subframe corresponds to a control region to which control channels are allocated, and the other remaining OFDM symbols correspond to a data region to which a physical downlink shared channel (PDSCH) is allocated.

The PDCCH may carry a transmission format and a resource allocation of a downlink shared channel (DL-SCH), resource allocation information of an uplink shared channel (UL-SCH), paging information on a PCH, system information on a DL-SCH, a resource allocation of an higher layer control message such as a random access response transmitted via a PDSCH, a set of transmission power control commands with respect to individual UEs in a certain UE group, an activation of a voice over internet protocol (VoIP), and the like. A plurality of PDCCHs may be transmitted in the control region, and a UE can monitor a plurality of PDCCHs. The PDCCHs are transmitted on one or an aggregation of a plurality of consecutive control channel elements (CCE). The CCE is a logical allocation unit used to provide a coding rate according to the state of a wireless channel. The CCE corresponds to a plurality of resource element groups. The format of the PDCCH and an available number of bits of the PDCCH are determined according to an associative relation between the number of the CCEs and a coding rate provided by the CCEs.

The BS determines a PDCCH format according to a DCI to be transmitted to the UE, and attaches a cyclic redundancy check (CRC) to the DCI. A unique radio network temporary identifier (RNTI) is masked on the CRC according to the owner or the purpose of the PDCCH. In case of a PDCCH for a particular UE, a unique identifier, e.g., a cell-RNTI (C-RNTI), of the UE, may be masked on the CRC. Or, in case of a PDCCH for a paging message, a paging indication identifier, e.g., a paging-RNTI (P-RNTI), may be masked on the CRC. In case of a PDCCH for a system information block (SIB), a system information identifier, e.g., a system information-RNTI (SI-RNTI), may be masked on the CRC. In order to indicate a random access response, i.e., a response to a transmission of a random access preamble of the UE, a random access-RNTI (RA-RNTI) may be masked on the CRC.

Figure 5:
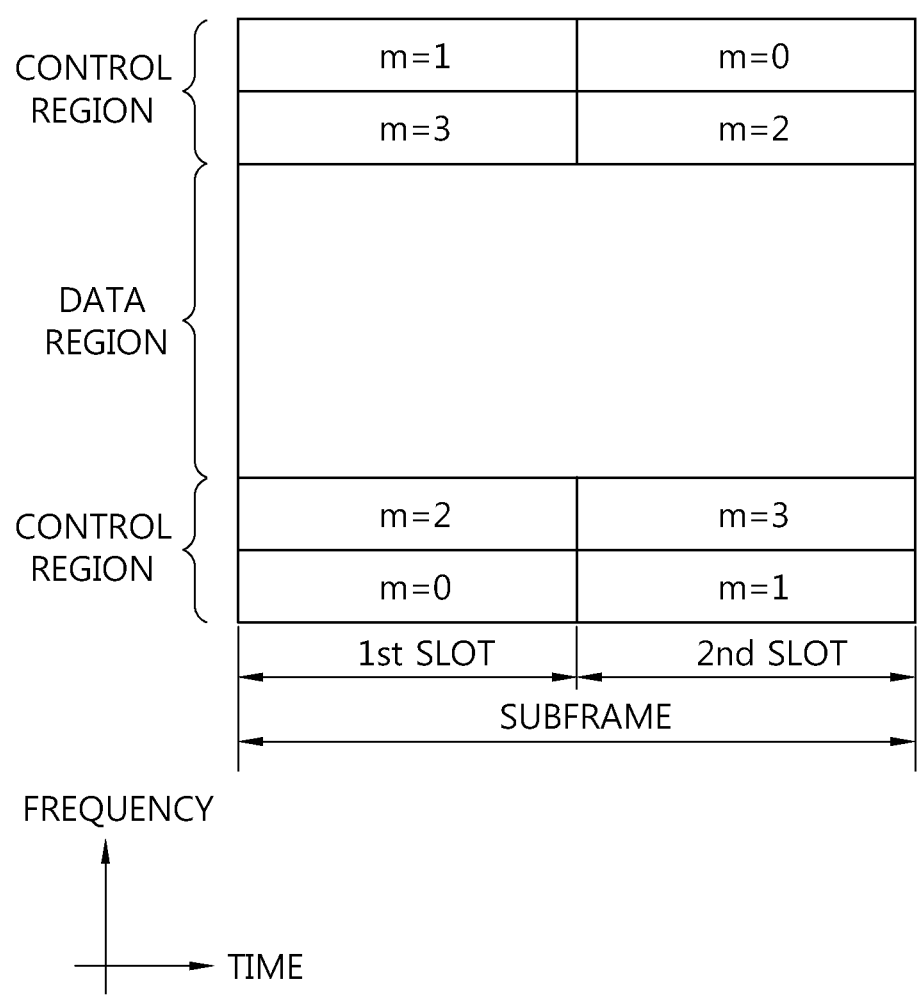
FIG. 5 shows the structure of an uplink subframe.

FIG. 5 shows the structure of an uplink subframe.

An uplink subframe may be divided into a control region and a data region in the frequency domain. A physical uplink control channel (PUCCH) for transmitting uplink control information is allocated to the control region. A physical uplink shared channel (PUCCH) for transmitting data is allocated to the data region. If indicated by a higher layer, the UE may support simultaneous transmission of the PUCCH and the PUSCH.

The PUCCH for one UE is allocated in an RB pair. RBs belonging to the RB pair occupy different subcarriers in each of a $1^{st}$ slot and a $2^{nd}$ slot. A frequency occupied by the RBs belonging to the RB pair allocated to the PUCCH changes at a slot boundary. This is called that the RB pair allocated to the PUCCH is frequency-hopped at a slot boundary. Since the UE transmits UL control information over time through different subcarriers, a frequency diversity gain can be obtained. In the figure, m is a location index indicating a logical frequency-domain location of the RB pair allocated to the PUCCH in the subframe.

Uplink control information transmitted on the PUCCH may include a HARQ ACK/NACK, a channel quality indicator (CQI) indicating the state of a downlink channel, a scheduling request (SR) which is an uplink radio resource allocation request, and the like.

The PUSCH is mapped to an uplink shared channel (UL-SCH), a transport channel. Uplink data transmitted on the PUSCH may be a transport block, a data block for the UL-SCH transmitted during the TTI. The transport block may be user information. Or, the uplink data may be multiplexed data. The multiplexed data may be data obtained by multiplexing the transport block for the UL-SCH and control information. For example, control information multiplexed to data may include a CQI, a precoding matrix indicator (PMI), an HARQ, a rank indicator (RI), or the like. Or the uplink data may include only control information.

Machine type communication (MTC) is one type of data communication including one or more entities that do not require an interaction with people. An MTC device refers to an MS installed for the MTC. An MTC device can communicate with an MTC server or can communicate with another MTC device. An MTC device may be called an M2M device. An MTC feature means a network function for optimizing a network used by an M2M device. An MTC server is an entity that communicates with a network and communicates with an MTC device over the network. An MTC server can have an interface accessible to an MTC user. An MTC server provides service for an MTC user. An MTC user uses service provided by an MTC server. An MTC subscriber is an entity having a contractual relation with a network operator in order to provide service to one or more MTC devices. An MTC group refers to a group of MTC devices that share one or more MTC features and belong to the same MTC subscriber. An MTC subscriber and an MTC group can be mixed and used.

Figure 6:
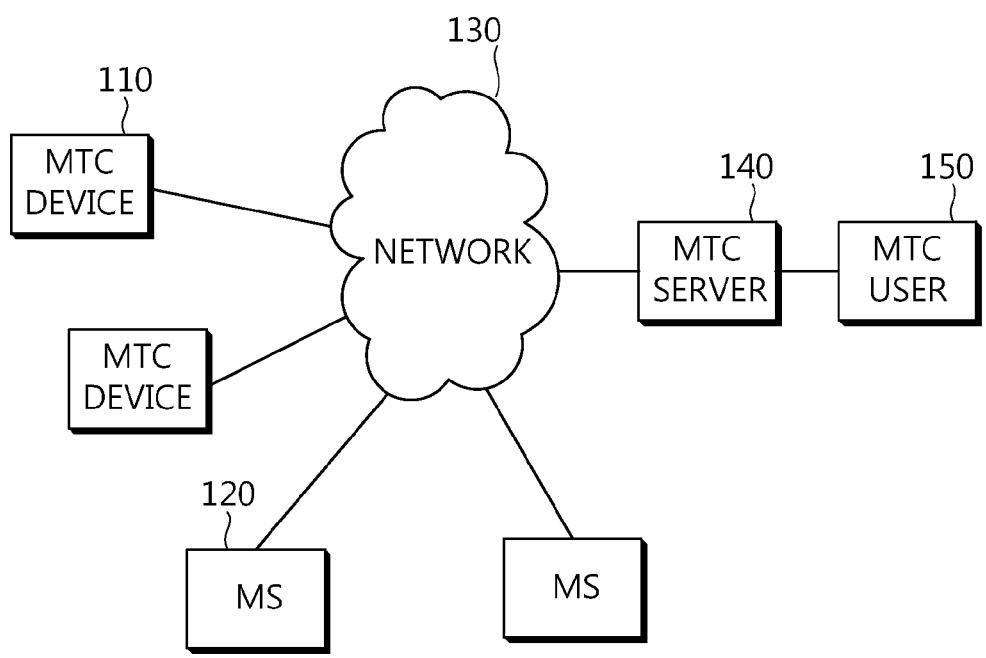
FIG. 6 shows an example of a communication scenario for MTC.

FIG. 6 shows an example of a communication scenario for MTC.

Referring to FIG. 6, an MTC device 110, together with an existing MS 120, is connected to a network 130. An MTC server 140 receives information from the MTC device 110 over the network 130 and provides the information to an MTC user 150. The MTC server 140 can be directly connected to the network 130, but may be connected to the network 130 through an Internet protocol (IP). The structure is only illustrative and can be changed in various forms. For example, the MTC device 110 can directly communicate with another MTC device without the MTC server 140. If the MTC device 110 is deployed in the network 130, a traffic load can be added to the network 130 depending on a traffic characteristic of the MTC device 110.

The MTC can be introduced into 3GPP LTE-A. In order for an MTC device to operate in an existing network, service requirements different from those of a legacy MS are necessary. The service requirements include common service requirements and specific service requirements. For the MTC service requirements of 3GPP LTE-A, reference can be made to Paragraph 7 of 3GPP TS 22.368 V10.0.0 (2010 March) "$3^{rd}$ Generation Partnership Project; Technical Specification Group Services and System Aspects; Service requirements for Machine-Type Communications (MTC); Stage 1 (Release 10)".

As M2M communication is introduced, a BS needs to couple many M2M devices and support scheduling the transmission of a small amount of data. Accordingly, UE-specific DCI for independently supporting the scheduling of M2M devices can be suddenly increased, which can result in overload for a downlink control channel. That is, there is a new method of transmitting a downlink control signal because additional overload is necessary for the downlink control channel if the downlink control signal is transmitted to many M2M devices through an existing DCI format in an M2M communication environment.

A proposed method of transmitting a downlink control signal is described below.

1) Persistent scheduling can be performed according to an M2M application in order to efficiently transmit a downlink control signal.

An M2M application for receiving and/or transmitting data for a very short time at a fixed place may be present and an M2M application for receiving and/or transmitting data relatively frequently while moving may be present depending on the type of M2M application. For example, an M2M application, such as a vending machine, may be in idle mode for the most of time and may exchange data with a BS for a very short time, and an M2M application related to consumer electronics or an automotive may exchange data with a BS frequently.

Figure 7:
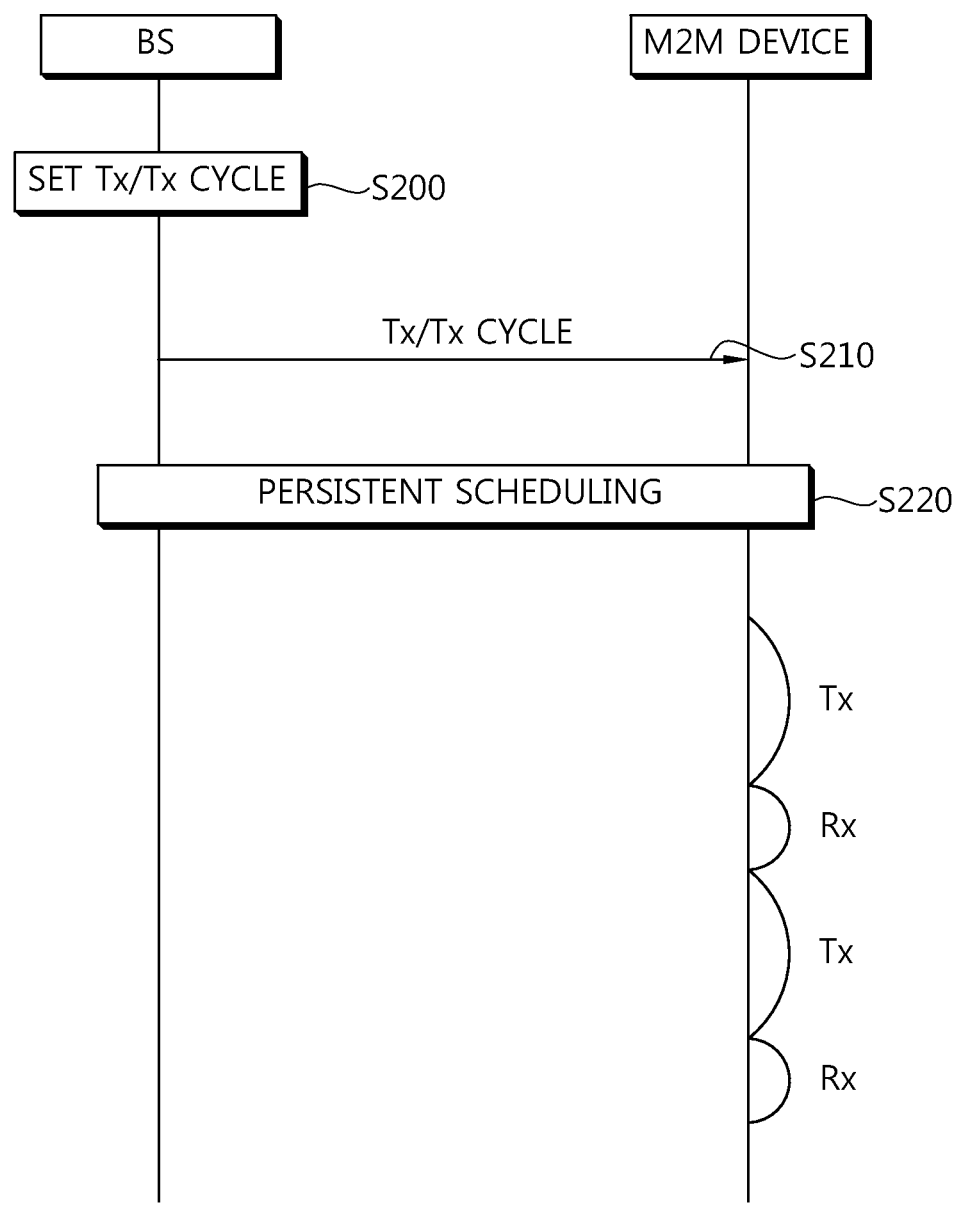
FIG. 7 shows an embodiment of a proposed method of transmitting a downlink control signal.

FIG. 7 shows an embodiment of a proposed method of transmitting a downlink control signal.

At step S200, a BS sets a transmission/reception (Tx/Rx) cycle $T_{SPS}$ depending on the type of an M2M application. At step S210, the BS transmits the set Tx/Rx cycle to an M2M device. At step S220, a persistent scheduling is performed on the M2M device based on the Tx/Rx cycle, and the M2M device can repeatedly transmit data to the BS and receive data from the BS although the M2M device is not scheduled again according to the set Tx/Rx cycle.

$T_{SPS}$ can be negotiated or requested by the M2M device according to an M2M application. $T_{SPS}$ can be L1/L2 control signaling or higher layer signaling. Furthermore, $T_{SPS}$ can be updated by higher layer signaling.

Furthermore, for a lower power consumption device, a discontinuous reception (DRX) cycle can be set along with persistent scheduling. An M2M device may not exchange any data with a BS during the DRX cycle. The DRX cycle can be implicitly set by $T_{SPS}$.

2) A reduced DCI format for efficiently transmitting a downlink control signal can be defined.

FIG. 8 shows an example of a reduced DCI format according to the proposed method of transmitting a downlink control signal.

FIG. 8(a) shows an example of an existing DCI format. The DCI format can include a frequency hopping flag, resource block assignment, a modulation and coding scheme (MCS), a transmission power control (TPC) command, a demodulation reference signal (DMRS) cyclic shift, a UL index, a downlink assignment indicator (DAI), etc. From among them, the MCS indicates a level according to a predetermined MCS, and a transfer rate can be determined by an MCS level. The MCS level can be determined by a signal to interference noise ratio (SINR), and a level having the highest efficiency can be selected as the MCS level based on the SINR.

FIG. 8(b) shows an example of a proposed reduced DCI format. The reduced DCI format does not include an MCS field. It may be assumed that an M2M device communicating with a BS at a fixed location or an M2M device communicating with a BS at a regularly generated traffic pattern does not experience a great change in a channel environment with the BS. In this case, information related to a channel environment, such as an MCS, does not have a great influence on communication between the BS and the M2M device although the information is not dynamically transmitted through a DCI format, but is semi-statically transmitted through higher layer signaling. The remaining pieces of information other than the information related to a channel environment are transmitted to the M2M device through the DCI format. In the present embodiment, information related to a channel environment has been illustrated as being an MCS, but is not limited thereto. For example, if information regarding transmission mode is included in an existing DCI format, the information may not be included in the reduced DCI format, but can be transmitted through higher layer signaling because it is expected that the transmission mode of an M2M device will not be greatly changed.

3) A group DCI format for efficiently transmitting a downlink control signal can be defined.

Various types of grouping can be performed on M2M communication. M2M service provider-based grouping and M2M subscriber-based grouping or M2M user-based grouping can be performed depending on an entity that performs M2M communication. M2M application-based grouping can be performed on M2M devices using the same M2M application, or M2M feature-based grouping can be performed on M2M devices having the same M2M feature. Or, M2M device location-based grouping or M2M channel status-based grouping can be performed. Or, hybrid type grouping having a combination of two or more of the above-described various grouping schemes may be performed. For example, M2M service provider-based grouping and M2M channel status-based grouping can be performed at the same time. One M2M group identifier (ID) can be assigned to a plurality of M2M devices bundled to one M2M group by way of the above-described various schemes.

FIG. 9 shows an example of a group DCI format according to the proposed method of transmitting a downlink control signal.

The group DCI format is transmitted to a plurality of M2M devices that belonging to the same M2M group. Referring to FIG. 9, the group DCI format includes a UE identification field, a group-common control information field, UE-specific control information fields, and a cyclic redundancy check (CRC). The group-common control information fields indicate control information in common that is applied to a plurality of M2M devices belonging to an M2M group. Each of the UE-specific control information fields indicates control information assigned to each M2M device. The UE identification field identifies an M2M device to which the UE-specific control information field is assigned. CRC is masked to an M2M group ID.

Furthermore, a group multicasting DCI format can be additionally defined. The group multicasting DCI format can include scheduling information about multicast information that is transmitted in common regarding a group. For example, the multicast information can include the upgrade of software or firmware, a group report request, etc.

Meanwhile, in many M2M applications, traffic patterns, such as a traffic volume and/or a traffic generation period, can be almost the same in M2M devices deployed according to specific service providers/subscribers/MSs. Furthermore, an M2M device type and capacity can be the same within a specific M2M application.

Accordingly, two-step resource assignment including first assigning group-common resources and then assigning M2M device-specific resources can be performed. In the first step group-common resource assignment, a DCI format can carry only information related to group-common resource assignment. UE-specific resource assignment information for the second step UE-specific resource assignment can be determined implicitly or explicitly. That is, a resource region in which each M2M device transmits or receives data traffic can be determined semi-statically.

Figure 10:
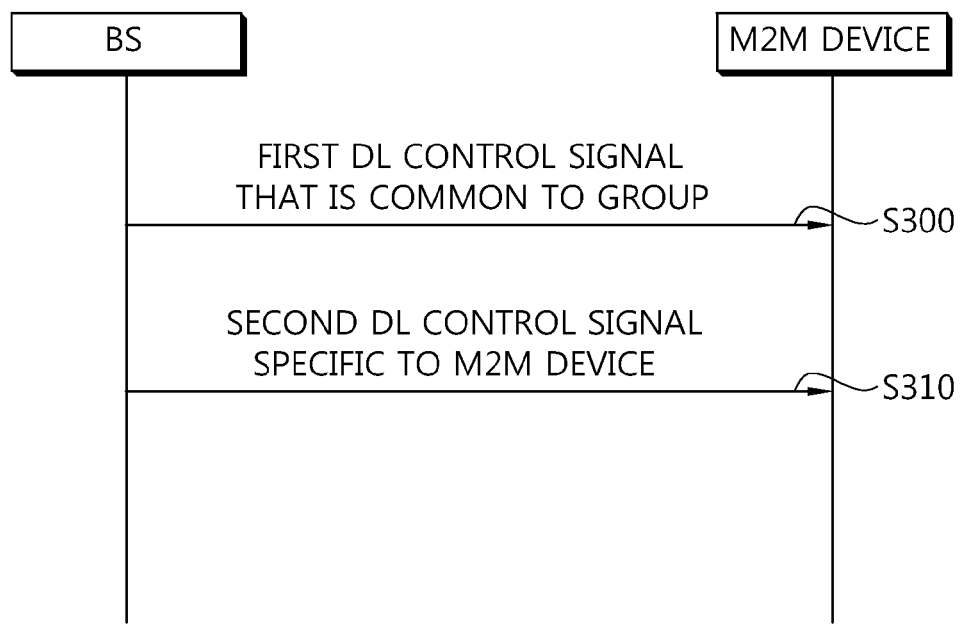
FIG. 10 shows another embodiment of a proposed method of transmitting a downlink control signal.

FIG. 10 shows another embodiment of a proposed method of transmitting a downlink control signal.

Referring to FIG. 10, a BS transmits a first downlink control signal assigned to an M2M group, including a plurality of M2M devices, to an M2M device included in the M2M group at step S300, and transmits a second downlink control signal, specifically assigned to the M2M device, to the M2M device at step S310. The first downlink control signal and the second downlink control signal can be transmitted through a group DCI format, or 2-step resource assignment may be performed based on each of the first and the second downlink control signals as described above.

Figure 11:
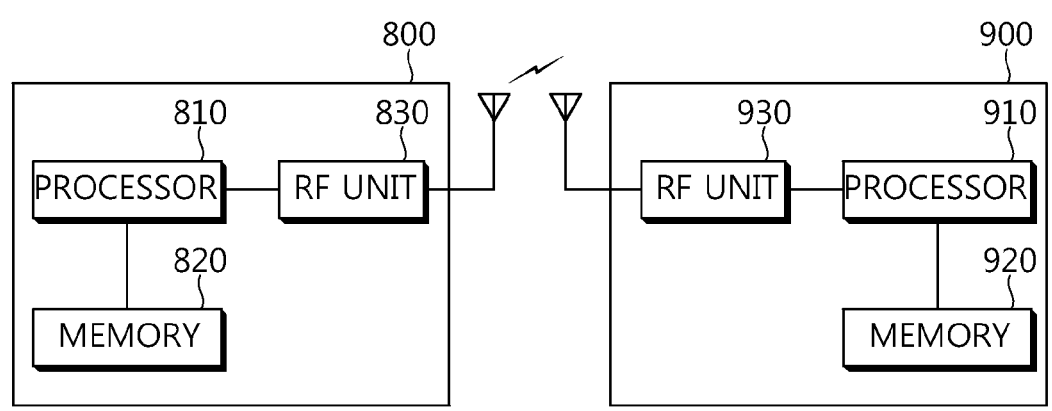
FIG. 11 is a block diagram showing wireless communication system to implement an embodiment of the present invention.

FIG. 11 is a block diagram showing wireless communication system to implement an embodiment of the present invention.

A BS 800 may include a processor 810, a memory 820 and a radio frequency (RF) unit 830. The processor 810 may be configured to implement proposed functions, procedures and/or methods described in this description. Layers of the radio interface protocol may be implemented in the processor 810. The memory 820 is operatively coupled with the processor 810 and stores a variety of information to operate the processor 810. The RF unit 830 is operatively coupled with the processor 810, and transmits and/or receives a radio signal.

A UE 900 may include a processor 910, a memory 920 and a RF unit 930. The processor 910 may be configured to implement proposed functions, procedures and/or methods described in this description. Layers of the radio interface protocol may be implemented in the processor 910. The memory 920 is operatively coupled with the processor 910 and stores a variety of information to operate the processor 910. The RF unit 930 is operatively coupled with the processor 910, and transmits and/or receives a radio signal.

The processors 810, 910 may include application-specific integrated circuit (ASIC), other chipset, logic circuit and/or data processing device. The memories 820, 920 may include read-only memory (ROM), random access memory (RAM), flash memory, memory card, storage medium and/or other storage device. The RF units 830, 930 may include baseband circuitry to process radio frequency signals. When the embodiments are implemented in software, the techniques described herein can be implemented with modules (e.g., procedures, functions, and so on) that perform the functions described herein. The modules can be stored in memories 820, 920 and executed by processors 810, 910. The memories 820, 920 can be implemented within the processors 810, 910 or external to the processors 810, 910 in which case those can be communicatively coupled to the processors 810, 910 via various means as is known in the art.

In view of the exemplary systems described herein, methodologies that may be implemented in accordance with the disclosed subject matter have been described with reference to several flow diagrams. While for purposed of simplicity, the methodologies are shown and described as a series of steps or blocks, it is to be understood and appreciated that the claimed subject matter is not limited by the order of the steps or blocks, as some steps may occur in different orders or concurrently with other steps from what is depicted and described herein. Moreover, one skilled in the art would understand that the steps illustrated in the flow diagram are not exclusive and other steps may be included or one or more of the steps in the example flow diagram may be deleted without affecting the scope and spirit of the present disclosure.

What has been described above includes examples of the various aspects. It is, of course, not possible to describe every conceivable combination of components or methodologies for purposes of describing the various aspects, but one of ordinary skill in the art may recognize that many further combinations and permutations are possible. Accordingly, the subject specification is intended to embrace all such alternations, modifications and variations that fall within the spirit and scope of the appended claims.

What is claimed is:

1. A method of transmitting a downlink control signal in a wireless communication system, the method comprising:

transmitting a first downlink control signal to a machine to machine (M2M) device included in a M2M group comprising a plurality of M2M devices, wherein the first downlink control signal relates to M2M group control information that is commonly assigned for all M2M devices included in the M2M group; and transmitting a second downlink control signal to the M2M device, wherein the second downlink control signal relates to specific M2M device control information that is assigned for only a specific M2M device in the M2M group, wherein the first downlink control signal and the second downlink control signal are transmitted using a group downlink control information (DCI) format, wherein the group DCI format comprises a field for a user equipment (UE) identification, a field for the M2M group control information, a field for the specific M2M device control information, and a field for a cyclic redundancy check (CRC), wherein the UE identification is used to identify the M2M device, wherein the CRC is used to mask an identifier (ID) of the M2M group, wherein the group DCI format further comprises a field for scheduling of multicast information that is commonly assigned to the M2M group, and wherein the multicast information relates to a message requesting a group report.

2. The method of claim 1, wherein the M2M group control information is configured for scheduling group-common multicast information assigned to the M2M group in common.

3. The method of claim 1, wherein the first downlink control signal is a DCI format comprising group-specific resource assignment information, and the second downlink control signal is determined implicitly or explicitly.

4. A machine to machine (M2M) device in a wireless communication system, the M2M device comprising:
    a radio frequency (RF) unit for transmitting or receiving a radio signal; and
    a processor connected to the RF unit, and configured for:
    receiving a first downlink control signal from a base station, wherein the first downlink control signal relates to a machine to machine (M2M) group control information that is commonly assigned for all M2M devices included in a M2M group; and
    receiving a second downlink control signal from the base station, wherein the second downlink control signal relates to specific M2M device control information that is assigned for only a specific M2M device in the M2M group,
    wherein the first downlink control signal and the second downlink control signal are received using a group downlink control information (DCI) format,
    wherein the group DCI format comprises a field for a user equipment (UE) identification, a field for the M2M group control information, a field for the specific M2M device control information, and a field for a cyclic redundancy check (CRC),
    wherein the UE identification is used to identify the M2M device,
    wherein the CRC is used to mask an identifier (ID) of the M2M group,
    wherein the group DCI format further comprises a field for scheduling of multicast information that is commonly assigned to the M2M group, and
    wherein the multicast information relates to a message requesting a group report.

5. The M2M device of claim 4, wherein the M2M group control information is configured for scheduling group-common multicast information assigned to the M2M group in common.

6. The M2M device of claim 4, wherein the first downlink control signal is a DCI format comprising group-specific resource assignment information, and the second downlink control signal is determined implicitly or explicitly.

7. A method of receiving a downlink control signal in a wireless communication system, the method comprising:
    receiving a first downlink control signal from a base station, wherein the first downlink control signal relates to M2M group control information that is commonly assigned for all M2M devices included in the M2M group; and
    receiving a second downlink control signal from the base station, wherein the second downlink control signal relates to specific M2M device control information that is assigned for only a specific M2M device in the M2M group,
    wherein the first downlink control signal and the second downlink control signal are received using a group downlink control information (DCI) format,
    wherein the group DCI format comprises a field for a user equipment (UE) identification, a field for the M2M group control information, a field for the specific M2M device control information, and a field for a cyclic redundancy check (CRC),
    wherein the UE identification is used to identify the M2M device,
    wherein the CRC is used to mask an identifier (ID) of the M2M group,
    wherein the group DCI format further comprises a field for scheduling of multicast information that is commonly assigned to the M2M group, and
    wherein the multicast information relates to a message requesting a group report.

8. The method of claim 7, wherein the M2M group control information is configured for scheduling group-common multicast information assigned to the M2M group in common.

9. The method of claim 7, wherein the first downlink control signal is a DCI format comprising group-specific resource assignment information, and the second downlink control signal is determined implicitly or explicitly.

* * * * *